United States Patent [19]
Kempe

[11] Patent Number: 5,897,838
[45] Date of Patent: Apr. 27, 1999

[54] APPARATUS FOR RAPID EVAPORATION OF AQUEOUS SOLUTIONS

[75] Inventor: Tomas Kempe, Bowie, Md.

[73] Assignee: Barrskogen, Inc., Washington, D.C.

[21] Appl. No.: 08/209,786

[22] Filed: Mar. 11, 1994

[51] Int. Cl.$^6$ .................................................. G01N 1/00
[52] U.S. Cl. ........................... 422/101; 422/99; 422/102; 422/103; 422/104; 436/177; 436/181; 435/287; 435/298
[58] Field of Search ............................ 422/99, 68.1, 101, 422/102, 103, 104; 436/177, 181; 435/287, 298

[56] References Cited

U.S. PATENT DOCUMENTS

| | | | |
|---|---|---|---|
| 3,219,099 | 11/1965 | Hamlow et al. | 422/101 X |
| 4,003,713 | 1/1977 | Bowser | 422/101 X |
| 4,346,057 | 8/1982 | Bower | 422/101 |
| 4,465,554 | 8/1984 | Glass | 159/16 R |
| 4,600,473 | 7/1986 | Friswell | 159/47.1 |
| 4,707,452 | 11/1987 | Friswell | 436/177 |
| 4,810,471 | 3/1989 | Wachob et al. | 422/103 |
| 4,908,319 | 3/1990 | Smyczek et al. | 435/285 |
| 5,100,623 | 3/1992 | Friswell | 422/68.1 |
| 5,176,799 | 1/1993 | Roe et al. | 202/185.3 |
| 5,217,572 | 6/1993 | Guy et al. | 159/6.1 |
| 5,282,927 | 2/1994 | Weidner | 159/147.1 |

OTHER PUBLICATIONS

Product description for Rotavapor™ RE–111 series, VWR Scientific.
Product description for Yamato Parkinson™ Freeze Dryer Model DC41–A, VWR Scientific.
Product brochure for CD8 model multipurpose freeze dryer, Heto Lab Equipment, Denmark.
Product description for Buchler™ vortex evaporator, Fisher Scientific.
Product description for Labconco™ RapidVap Models 16–317–1 and 16–317–3.
Product description for DNA SpeedVac™ instrument (Savant model DNA110).
Product description for centrifugal evaporator (Jouan™ models RC 10.10 and RC 10.22).
Product brochure for speed vacuum concentration system (HETO™ models HS–1–60 and HS–1–110).
Product brochure for blow–down unit (Zymark™, "TurboVap LV").

*Primary Examiner*—Harold Y. Pyon
*Attorney, Agent, or Firm*—Fredrikson & Byron, P.A.

[57] ABSTRACT

A simple, convenient and inexpensive apparatus for the concentration or evaporation of aqueous solutions typically used in biomedical research and development. The apparatus involves the use of a combined vacuum and blow-down effect, optionally including the application of heat. Using the apparatus a vacuum, as can be provided by a common water aspirator, serves the multiple purposes of facilitating the evaporation, creating the blow-down effect, and flushing the evaporated solvent from the system.

10 Claims, 2 Drawing Sheets

APPARATUS FOR RAPID EVAPORATION OF AQUEOUS SOLUTIONS

TECHNICAL FIELD

The present invention relates to apparatuses and processes useful for concentrating or evaporating solvent solutions, such as the solutions used in biomedical laboratories for the recovery of biopolymers such as DNA, RNA, peptides, proteins and saccharides.

BACKGROUND OF THE INVENTION

There are several options presently available for use in concentrating solutions used in biomedical research and development. The solutions are aqueous in many instances, but may also frequently contain organic solvents that are miscible with water. Evaporation of organic solvents having low boiling points can often be performed using a standard "rotavapor" type device. Solvents having higher boiling points are typically removed by the use of distillation apparatuses. (e.g., a rotavapor of the RE-111 and RE-121 series, as are available from Buchi/Brinkmann through VWR Scientific).

Methods commonly used to remove water from solutions containing biopolymers typically involve lyophilization or freeze drying. For instance, such methods commonly employ a multipurpose freeze-drying apparatus such as that available from VWR Scientific as the Yamato Parkinson Freeze Dryer Model DC41-A, and the CD8 model multipurpose freeze dryer available from Heto Lab Equipment, Denmark. In such a method the sample is frozen in a tube or a flask, and a vacuum is applied. The removal of water is then performed from a solid state (e.g., ice) into a receiving flask, which is also cooled to collect the water vapor.

When an aqueous solution also contains an organic solvent that is miscible with water, it may not be possible to perform a lyophilization procedure, particularly if the mixture does not solidify upon cooling. In this case a number of other evaporation techniques can be used. Such a solution can be subjected to a vacuum, as described above, under conditions that prevent the sample from "bumping" (i.e., boiling in a manner that causes the solution to splash rapidly).

The solution can then be agitated or rotated to generate a centrifugal force. Agitation can be performed using, for instance, a Buchler vortex evaporator (e.g., model 09-548 available from Fisher Scientific, or Labconco RapidVap Models 16-317-1 and 16-317-3). Rotation can be performed using an instrument such as a New DNA SpeedVac instrument (e.g., Savant model DNA110, Jouan models RC 10.10 and RC 10.22, HETO models HS-1-60 and HS-1-110). Instruments of the former type provide a combination of gyrating motion, heat, and either vacuum or blowdown. Instruments of the latter type are generally referred to as centrifugal concentrators and are among the most common evaporators in laboratories.

With both types of evaporators, the evaporation process is generally facilitated by the use of a heating source, in fact, the vacuum chamber generally includes a thermostat-controlled heating device.

The vacuum needed to use such evaporators is typically provided by the use of a high-vacuum pump (e.g., HETO RZ 2 type) that is capable of generating pressure down to at least 1 mm Hg. Such pumps are often oil-type pumps that must be protected from solvents and water by the use of cooling traps (e.g., HETO CT60e type), in order to condense the evaporated solvent before it reaches the oil. Alternatively, such a pump can be a diaphragm-type that does not require the use of oil, but which typically does not generate as much vacuum (for instance, down to 10–20 mm Hg), thereby requiring longer evaporation times.

A simple evaporation process can be achieved by the use of a heating block such as the "Reacti-Therm" dry block available from Pierce as product #18800/18801. In such a process a tube containing a sample is inserted into a block that can be heated to a desired temperature.

A more efficient evaporation is achieved in the heated block if a gas is streaming through to carry the gaseous solvent with it. These types of evaporators are commonly called blow-down evaporators (Pierce, Reacti-Vap evaporator #18780). Examples of such evaporators include hot-blocks from Pierce and hot-block/blow-down combinations as described above. A type of blow-down unit has recently become available from Zymark ("TurboVap LV"). This unit involves the use of air or gas fed into a tube that is kept in a water-bath, in order to generate what is described as a gas vortex shearing technique.

The evaporation units presently available, however, generally continue to encounter significant drawbacks. Generally, the evaporation units that are the least expensive and easiest to use are the same units that require the longest evaporation times, or have other associated drawbacks. In contrast, the more expensive and technically complicated units are often unnecessary for simple procedures and cost-prohibitive for many labs.

What is clearly needed is an evaporation unit that provides an optimal combination of cost, ease of use, and efficiency for evaporating aqueous solvents commonly encountered in biomedical research.

SUMMARY OF THE INVENTION

Figure 1:
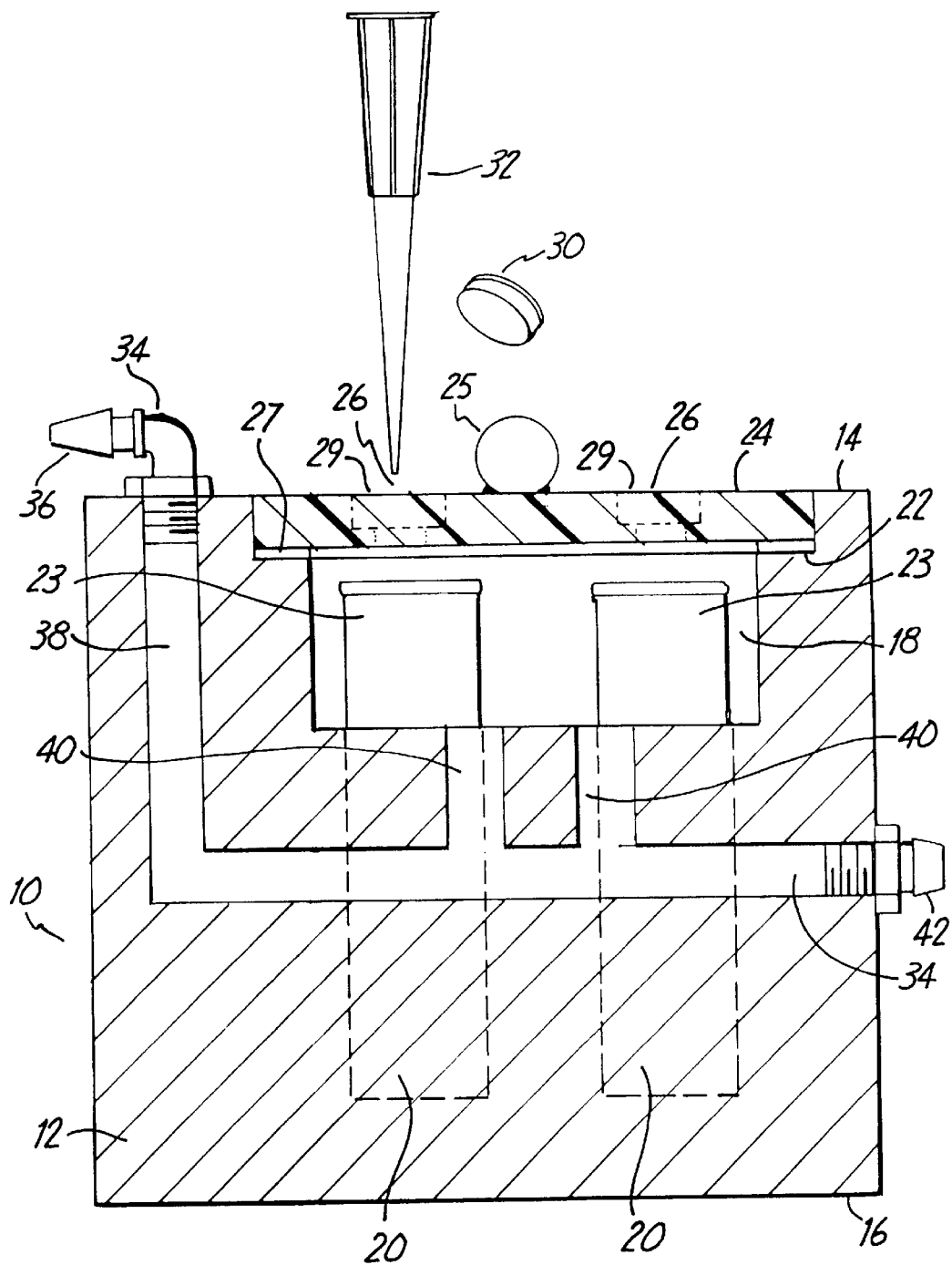
FIG. 1 shows a cross-sectional of a preferred evaporating unit of the present invention.

The present invention provides a simple, convenient and inexpensive apparatus for the concentration or evaporation of aqueous solutions typically used in biomedical research and development.

In particular, the invention provides an apparatus useful for evaporating solvents from a plurality of solvent-containing sample vials, the apparatus comprising:

(a) a substantially heat-transmissive block having a top surface comprising a sample chamber, the chamber comprising a plurality of well positions dimensioned to releasably hold sample vials in an upright, stable retained position within the chamber, (b) a positionable chamber cover dimensioned to form a substantially air tight seal when in a closed positioned upon the chamber, the cover comprising a plurality of access apertures, each dimensioned to receive a respective air channeling device and positioned to lay in substantially overlapping position with a respective well position when the cover is positioned upon the chamber, and (c) a vacuum circuit comprising a vacuum source attachment site associated with the block and a vacuum passageway operably connecting the source attachment site with the chamber, whereby, with solvent-containing vials in position within the chamber and air channeling devices in position within the apertures of the cover, and with the cover in position upon the chamber, then upon attachment of a vacuum source to the vacuum source attachment, a vacuum can be drawn in the sample chamber in such a manner that air or other desired gas is correspondingly drawn through the air channeling devices such that air flow is directed toward the vial positions below in order to provide a blow-down evaporative effect.

In spite of its simplicity, an evaporator unit of the present invention provides remarkable improvement in terms of the time necessary for the evaporation of aqueous and organic solvents commonly used in biomedical research. For instance, the evaporation of 1 ml of methanol/water (50/50 by volume) is completed within about eight minutes at 75° C.

In comparison, the evaporation of the same sample using a TurboVap LV (Zymark) laboratory rotary evaporator requires on the order of 12 minutes, even though this particular type of evaporator is generally considered to be among the fastest presently available for such purposes. Many other commercial instruments, including those costing far more, require even greater times (e.g., up to two hours) for evaporation of such samples.

The evaporator unit of the present invention is particularly well suited for use with the cleavage and deprotection steps involved in the processing of biopolymers such as synthetic nucleic acids. It is useful, for instance, for the fast removal of ammonia following the cleavage and deprotection steps involved in processing synthetic DNA. For use with synthesized DNA, for instance, that temperature will generally be set between about 55° C. and 85° C. Depending on the synthetic methodology employed, one will typically need to evaporate either ammonium hydroxide resulting from synthetic DNA or DMT-DNA processes, or acetonitrile/water mixtures resulting from high pressure liquid chromatography ("HPLC") and cartridge-purified DNA.

Such applications can be facilitated by the use of blocks that are dimensioned to accept the size and types of tubes commonly used in such procedures, and that are themselves dimensioned to be placed in or on commercially available heating devices.

DETAILED DESCRIPTION OF THE INVENTION

The present invention provides a simple and inexpensive apparatus for concentrating or evaporating aqueous solutions typically used in biomedical research and development. It has been discovered, for instance, that a simple principle of combining vacuum and blow-down in the manner presently claimed, with the optional inclusion of heat, provides a powerful evaporation technique not previously disclosed or used in the field of chemical, biopolymer, or DNA/RNA processing.

A preferred embodiment of the present invention will be described with reference to the Drawing, beginning with FIG. 1. The invention provides an apparatus 10 useful for evaporating solvents from a plurality of solvent-containing sample vials, the apparatus comprising a substantially solid block 12 having top 14 and bottom 16 surfaces, the block being constructed of substantially heat-transmissive material. Top surface 14 of the block comprises a recessed sample chamber 18.

Chamber 18, in turn, comprises a plurality of recessed well positions 20 dimensioned to releasably hold sample vials (shown as 23) in an upright, stable retained position within the chamber. In order to optimize the uniform heating of vials, the wells are preferably dimensioned such that vials will be surrounded by and in contact with the block material at all but their uppermost surfaces. In a preferred embodiment standard laboratory vials are used that are is 15 mm in outer diameter and 45 mm high, having a capacity of 4 ml solvent. Chamber 18 further comprises a recessed rim 22 at the block top surface 14.

Apparatus 10 further comprises a removable cover 24 dimensioned to form a substantially air tight seal when positioned within the recessed rim 22 of the chamber 18. Optionally, and preferably, a suitable gasket 27 of similar sealing material is used between and on either the cover, the chamber rim, or both, in order to facilitate the formation of a vacuum-tight seal.

Cover 24 comprises a handle 25 as well as a plurality of access apertures 26, each positioned to lay in substantially overlapping position with a respective well position 20 when the cover is positioned within the recessed rim of the chamber. The apertures can be used in any suitable manner in order to allow the delivery of a stream of gas to the vial beneath. The effective diameter of each aperture is preferably adjustable, in the manner described herein, in order to allow a variety of blow-down gas channels or conduits to be inserted therein.

In a preferred embodiment, apertures are configured such that they are surrounded by a concentric region 29 countersunk in the top surface of the cover. The countersunk regions are positioned and dimensioned in order to releasably retain rubber septa through which needle tips (e.g., standard disposable 16 to 27 gauge) can be inserted and retained. With the needles in place, the cover can be positioned on the chamber such that each needle tip extends through the septa 30 and apertures and into or above a respective vial. Upon application of a vacuum the gas flows from either the ambient atmosphere, or from an external source of desired gas, through the needles and into the vials.

In an alternative preferred embodiment, standard disposable pipette tips (e.g., 50 to 200 microliter, shown as reference number 32) can be inserted into the cover apertures (without the inclusion of septa) and there retained in position as the cover is repositioned above the chamber. Upon application of a vacuum, gas is again able to flow through the pipette tips in order to achieve a similar result. As with the needles, the pipette tips can then be properly disposed in order to avoid any chance of cross-contamination of samples.

Apparatus 10 further comprises a vacuum circuit 34 comprising a vacuum source attachment site 36 associated with the block and a vacuum passageway 38 operably connecting the source attachment site with the chamber. Passageway 38 extends into the chamber by means of vacuum inlets 40 on the inner surface of chamber 18. Passageway 38 terminates with air-tight plug 42 on the opposite surface of the block.

The above-described configuration for the vacuum passageway facilitates the manufacture of such a block. The passageway can be created by drilling one hole from the top of the block, alongside the chamber, to approximately the midpoint of the block (i.e., to a point beneath the depth of chamber 18). Following that, a joining passageway can be drilled through the side of the block and directly under the passageway. The joining passageway portion can be tapped into the chamber by drilling one or more smaller holes through the base of the chamber, and can be closed off by the use of air-tight plug 42 or any other suitable means.

In operation, the apparatus 10 is generally first attached to a vacuum source by means of attachment site 36. Cover 24 is then removed in order to allow the user to position sample vials within one or more of well positions 20. Thereafter, the cover 24 is replaced in its position within the recessed rim 22 of chamber 18. Gas channeling devices are inserted through the apertures in the desired manner. A vacuum source is operably attached to vacuum attachment site 36 and a vacuum is drawn through passageway 38 and, in turn, in chamber 18.

As the vacuum source is begun a vacuum is created within the chamber, which in turn, draws air or gas through the air channeling devices within cover apertures 26. Preferably, the gas flowing through each aperture is directed to the desired position within or above each respective vial. The gas flow through the apertures and into the vials, in turn, provides a blow-down evaporative effect. Since a vacuum is being applied, the air or inert gas will simultaneously flow through the needle and agitate the solution, being drawn by the vacuum itself. As the gas is eventually drawn back out of the vial and through the passageway by continuing vacuum effect, it will tend to also carry the evaporated solvent vapors with it.

With an otherwise air-tight evaporator block, those skilled in the art will be able to accurately control and adjust the time necessary to evaporate any particular volume and type of solvent by choosing an optimal combination of the temperature, the strength of vacuum pulled within the chamber, and the type, size and location of channeling devices within or above the vials.

When the evaporation is completed, the vacuum source can be turned off in order to allow the chamber interior to return to atmospheric pressure. Cover 24 can then be removed, needles or pipette tips can be disposed of, and the vials removed from within the chamber.

Optionally, and preferably, block 12 is heated to a desired temperature while the block is in use, in order to facilitate the evaporation process. In view of the heat-transmissive nature of block of the present invention any suitable heat source can be used to heat the block, and in turn the chamber interior, to the desired extent.

An aluminum block as disclosed in this invention can be heated by many different devices, for instance, it can be fitted with a thermostat-controlled heating blanket and put into an enclosure as a stand alone evaporation unit. Alternatively, the block can be placed into a water-bath at the desired evaporation temperature, or placed on a hot plate of any type suitable to perform evaporation (as are commonly available, for instance, from VWR Scientific).

Figure 2:
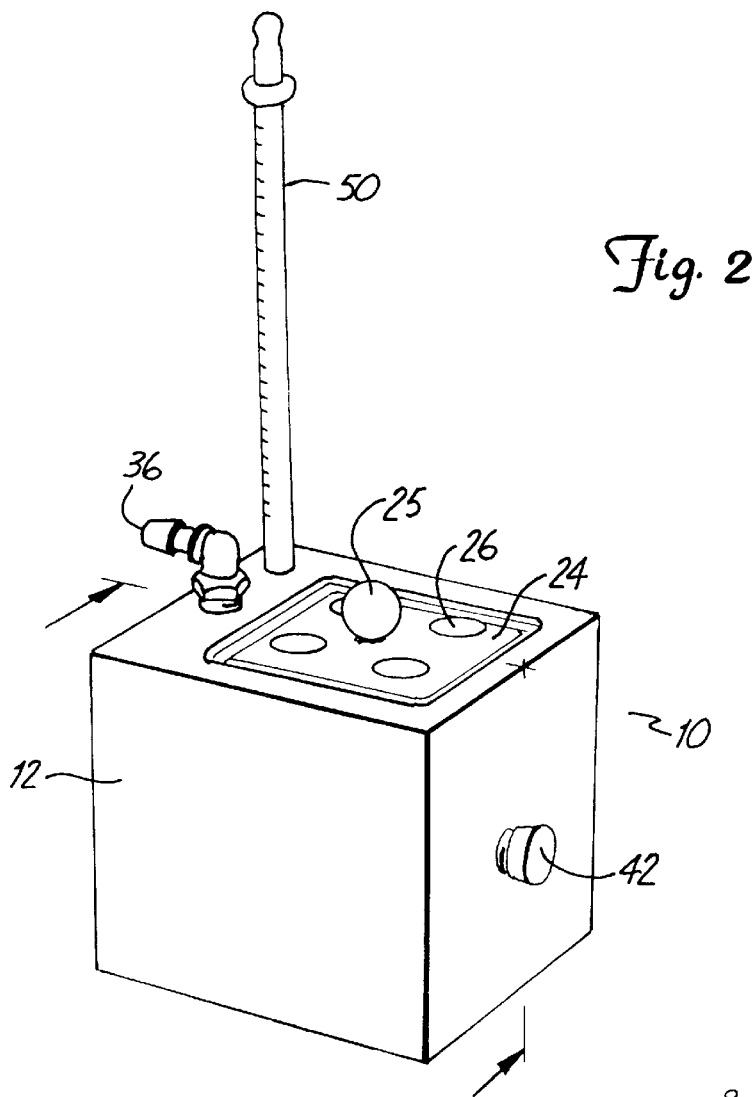
FIG. 2 shows a perspective view of the unit of FIG. 1.
Figure 3:
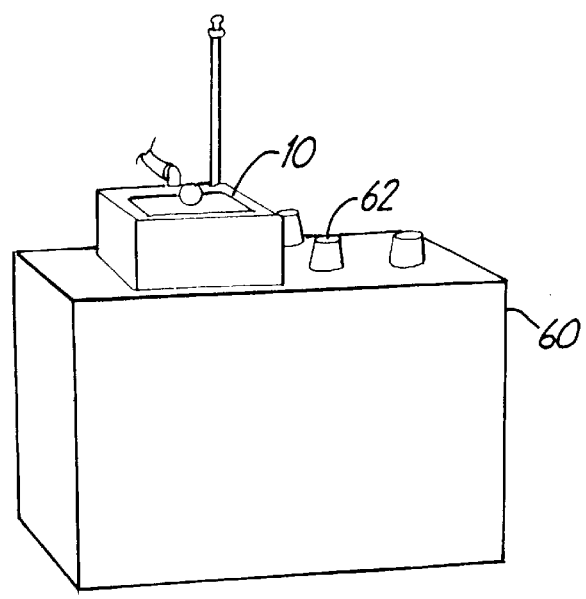
FIG. 3 shows a perspective view of the unit of FIG. 1 situated within a heating block.

With reference to FIGS. 2 and 3 of the Drawing, an apparatus of the present invention can be seen in use. In FIG. 2, apparatus 10 can be seen in perspective view with cover 24 in place (shown with septa covering each aperture). A preferred block of the present invention further comprises a temperature sensing device, such as a thermometer receptacle drilled within the block. When a thermometer is inserted into the receptacle, it can be used to assess and control the evaporation temperature. As shown in FIG. 2, thermometer 50 in placed within a receptacle drilled within the top surface of block 12.

In turn, FIG. 3 shows the apparatus in position within a heating device 60 such as described herein. Heating device 60 is typically electrically powered, and provides adjustment knobs 62 for controlling the temperature of the heating block receptacle. A number of heating devices can be used to provide heat to a block of the invention, for instance, the block can be equilibrated in a water bath at a set temperature, or the block can be placed into the bath after samples and cover has been put on. The evaporation will typically proceed more quickly if the block has first been equilibrated to evaporation temperature.

A preferred block of the present invention is dimensioned to allow it to be placed within a heating unit of the type commercially available as (e.g., VWR heat block, model 13259-005). In this manner the laboratory technician can take advantage of equipment than may already exist in the laboratory. Using a heating block available through VWR Scientific as catalogue number 13259-005, a calibration curve can be easily constructed to establish the approximate settings of the low and/or high temperature adjustment settings in order to equilibrate the block to any desired temperature between 35° C. and 90° C. For instance, a block was equilibrated to 55° C. in such a heating unit by setting the low setting at 6 for 30 minutes, whereas the block was equilibrated to 75° C. within 45 minutes with the low setting at 8.5.

The evaporation can be performed by allowing ambient air flow through the system. If however an inert gas is required, e.g., in order to avoid oxidation of the sample such as peptides with methionine or tryptophane amino acids, the air can be replaced with a source of inert gas such as helium, nitrogen, argon or the like. For instance, needles fitted with a female luer fitting can be connected to a manifold with male luer fittings and be connected to a gas cylinder for that purpose.

The flow rates through the system can be adjusted within a wide range. A range of 100 ml/min up to 20 liter/min are acceptable flow rates. The flow rates used in the examples below were typically in the range about 1 liter/min to about 10 liter/min. The vacuum generated within the chamber can be controlled by the capacity of the vacuum source and the restrictions generated by the needles bleeding gas into the vacuum chamber. The needle inner diameter can be of any size suitable for an evaporation and can be chosen from commercially available needles also, which comes in 16 gauge to 27 gauge. As a result, the vacuum can be varied substantially from about 10 mm Hg up to near atmospheric pressure of about 750 mm Hg.

As an additional benefit, disposable needles or pipette tips as are commonly available in most laboratories can be used as gas channeling devices with the present system. Moreover, they can be changed after each operation to prevent cross contamination of samples. The flow rate through the system can be varied by different size needles and vacuum sources in order to fit a particular evaporation routine deemed necessary by the user.

An evaporation system having the characteristics of both a vacuum evaporator and a blow down evaporator for fast, cheap evaporation of aqueous solutions typically used in DNA, RNA, peptide and oligosaccharide work. In particular, a preferred apparatus provides a number of desirable options, including:

efficient evaporation by the use of simple low vacuum device such as water aspirators and diaphragm pumps.

the use of an apparatus as a stand alone unit with heating device built in.

the use of the apparatus in a water bath, on a hot plate, in an oven, or even irradiated by a heat lamp or other suitable source in order to achieve external heating for speeding up the evaporation.

the apparatus can be pre-heated and left at room temperature in order to use residual heat in the system for the evaporation.

the apparatus is particularly well-suited for reduced odor, or odor-free evaporation at the laboratory bench.

the apparatus can also be cooled in order to be used in lyophilization procedures.

The evaporation device of the present invention is particularly useful for processing synthetic DNA and RNA molecules. After the completion of synthesis an oligonucleotide is typically cleaved from its support by adding concentrated ammonia. The cleaved oligonucleotide can then be deprotected at between 55° C. and 85° C. to remove protecting groups on the purine and pyrimidine portion of the molecule. This operation is relatively fast with present-day reagents and synthesizers.

A typical synthesis and work-up routine involves the following steps: synthesis (1 hour), cleavage from column (1 hour), deprotection using standard reagents (5–10 hours, although the use of sensitive protecting groups can reduce the deprotection time to less than 15 minutes). Lastly, the evaporation of solvents, using a standard centrifugal evaporator, generally requires on the order of 2 to 3 additional hours.

In a particularly preferred embodiment the apparatus is useful for the concentration of solutions containing DNA or RNA following cleavage/deprotection or purification of the molecules. The apparatus is particularly well adapted for the purpose of rapid evaporation of ammonium hydroxide and mixtures with organic solvents or acetonitrile and aqueous acetonitrile mixtures and alike or any solution suitable to be concentrate on the device.

A preferred vacuum source for use with the present apparatus is the standard laboratory water-aspirator. Solvent vapors can be collected in a cooled vacuum trap (e.g., Kontes KT 926250-0021) kept in a Dewar flask (e.g., 350 ml capacity VWR Cat. No. 63422-028) containing dry ice. By use of the present apparatus, an inexpensive water-aspirator can be sufficient to evaporate at a speed as fast as, or often faster than, the speed possible with more expensive, e.g., centrifugal, evaporators. The rate of evaporation can also be controlled by the heat input into the system. Generally speaking, the heating of sample vials will typically have a greater impact on the evaporation speed than will the flow through speed of the gas.

The disclosed evaporation device reduces the time-consuming evaporation step at a fraction of the cost of conventional systems. An evaporation procedure that once required 2 to 3 hours to perform can now be completed in 10 to 15 minutes.

Another common preparative procedure in oligonucleotide chemistry involves what is known as cartridge purification. This procedure typically requires the evaporation of a 20% aqueous acetonitrile mixture in order to recover the biomolecule. Using an apparatus of the present invention, such evaporation can be accomplished as quickly and economically as the above-described ammonia evaporation.

Similarly, high pressure liquid chromatography ("HPLC") isolates, which often contain acetonitrile and ammonium acetate, can be evaporated and peptide samples containing acetonitrile trifluoroacetic acid evaporated as well.

As an added feature of the apparatus of the present invention, the solutions do not need to be completely dried in order to be used. For example, ammonia evaporation generally must proceed to completion, since residual ammonia may interfere with subsequent operations. An apparatus of the present invention partial evaporation, in combination with the blowing of air or inert gas over the sample, can be used to effectively de-gas the ammonia containing solution. As a result, the residue of a 100 microliter sample of ammonia will typically demonstrate a pH of only about pH 7 to 8. This pH will likely be acceptable for subsequent preparative steps.

Another advantage of the apparatus of the present invention arises in the fact that complicated, expensive vacuum pumps are not necessary in order to achieve fast evaporation. The vials used in with the apparatus are those typically adapted to biopolymer processes, e.g., having volumes of about 1 to about 5 ml, such as those used for DNA deprotection with ammonia and cartridge purifications of DNA. Using such vials and volumes, the use of a water aspirator has been found to be sufficient for the removal of ammonia by dissolving it in the water used for aspiration. The combination of vacuum and blow-down effect can therefore allow for odor-free evaporation at the bench. Furthermore the size of the unit is small and can be used on an existing heating device in the laboratory (water bath or similar).

A preferred apparatus of the present invention will typically have at least four well positions. The use of a particular evaporator can thus be dedicated to a single DNA, since the evaporator will have the capacity to accept all vials coming off of the synthesizer, yet the cost of the evaporator will not be prohibitive. This, in turn, tends to streamline and facilitate the operation of such laboratories.

An apparatus of the invention was constructed of aluminum and other materials in the following manner. An aluminum block was cut measuring 3 (width)×3 (height)×3¼ (length) inches. A plexiglass cover was cut measuring 2¼×2¼×¼ thick inches. A round plastic handle was glued to the center of the cover and four apertures were drilled in the cover, each 3 mm in diameter. Each aperture was centered within a countersunk septa region 12 mm in diameter. A recessed rim was created on the block by countersinking the edge of the chamber by ¼ inch. A rubber gasket ("Buna-N") fitting the recessed rim was prepared to be ⅛ inch (3 mm) thick.

Within the chamber, four wells (15 mm in diameter and 1 and ½ inch deep) were positioned equidistant on the bottom of the chamber, in order to receive four standard laboratory vials. A channel to serve as the vacuum passageway was drilled through the base of the block from one side to the other, and an other channel was drilled across and between the cavity for the vials in order to connect with the other channel. The bottom of the chamber had two holes connecting the channel below, both of which were ¼ inch diameter.

The vertical channel was equipped with a fitting for a vacuum hose; L-shaped fitting with ⅛-27 NPT thread and barb for 3⁄16 inch tubing, Value Plastic, Fort Collins Colo., 18L250-1, white nylon. The vertical channel was fitted with a plug at the end, Value Plastic, 1800-1, ⅛-27 NPT plug, white nylon.

A vacuum hose latex tubing, VWR 62996-440, I.D. 3⁄16 inch, wall 3⁄32 inch was connected to the L-shaped fitting. A water aspirator VWR, polypropylene, 28610-008 was connected to a faucet and the tubing attached to it. Vials for the cavity were SRI brand 78315-C, 15 mm in diameter, step vials, 15×45 mm, borosilicate, 4 ml. Four septa were obtained (SRI 80415-S, silicone/PTFE) each 75 mil, 12 mm in diameter. A diaphragm pump was optionally used as a vacuum source, obtained from VWR, AirCadet pump, BR 7530-40. At times disposable needles were used (Becton-Dickenson disposable needles 1.5 inches long, 18 to 22 Gauge).

An apparatus of the present invention was manufactured for a fraction of the cost associated with the more common centrifugal evaporators. It is estimated that both an evaporator block of the present invention and an associated heating device can both be manufactured and sold for a total of less than about $1,000. In comparison, presently available commercial evaporation systems presently cost between about $6,000 and $10,000. Yet, the speed of evaporation using an apparatus of the present invention can often be as fast as, or even 10 to 15 times faster than, the speed possible using centrifugal evaporators. In fact, the speed possible with a block of the present invention is similar to the speed possible using a device such as the TurboVap LV (Zymark), which can cost over $6,000.

EXAMPLES

The apparatus of the present invention will now be further described by the following non-limiting examples. While only certain embodiments of the present invention are described in specific detail, it will be apparent to those skilled in the art that many other specific embodiments may be practiced and many changes made, all within the spirit of the invention and the scope of the appended claims.

Example 1

A standard 4 ml vial (15×45 mm) was filled with 1 ml of methanol/water (50/50 by volume). Using an aluminum block of the present invention having four cavities dimensioned to receive such vials, the vial was placed into one of the cavities. Vacuum tubing was connected to the evaporator and to a diaphragm pump. The cover was placed on the unit and a 22 G needle was inserted through the septa/cover into the vial. The pump was started and the block was placed into a water-bath at 85° C., 2 inches deep. The evaporation was terminated after 12 minutes at which time the vial was removed and found to be completely dry. For vials containing biopolymer the biopolymer can then be resuspended and used.

Example 2

Two vials were filled with 1 ml of concentrated ammonium hydroxide each. The vials were inserted into two cavities within the chamber of an evaporator block, the vacuum tubing was connected to the evaporator and diaphragm pump. The cover was put on the unit and 22 G needles were inserted in the septa above the vials all the way into the vial mouth.

The pump was started and the block was put into a water bath at 75° C., 2 inches deep. The evaporation was terminated after 12 minutes and the vials were dry.

Example 3

When the experiment described in Example 2 was performed using a water aspirator, the evaporation was complete in 15 minutes.

Example 4

When the experiment described in Example 2 was performed at 55° C. the evaporation was complete in 20 minutes.

Example 5

When the experiment described in Example 2 was performed using a water aspirator at 55° C., the evaporation was complete in 30 minutes.

Example 6

When the experiment described in Example 2 was performed using 20% aqueous acetonitrile, the evaporation rate was the same as for concentrated ammonium hydroxide described in EXAMPLE 2–5.

Example 7

A number of solvents typically used in DNA and peptide synthesis were evaluated in the evaporator block of the present invention. Low boiling solvents (e.g., dichloromethane, which boils at 40° C.) can be easily and effectively evaporated using the device. It is particularly noteworthy that such solvents could be evaporated without "bumping", or therefore loss of the contents, without the need for centrifugal force, as is commonly applied in the use of alternative techniques. The balance that is provided by the evaporator block, between blow-down and moderate vacuum, makes even the evaporation of low boiling solvents possible. One ml of dichloromethane was evaporated in about 1 minute at 65° C.; 1 ml of 2-propanol was evaporated in about 2 minutes at 55° C.; 1 ml of 80% aqueous acetic acid in about 3 minutes at 55° C.; 1 ml of trifluoroacetic acid was evaporated in about 2 minutes at 35° C.; and 1 ml of acetonitrile was evaporated in about 2 minutes at 35° C.

What is claimed is:

1. An apparatus useful for evaporating solvent from a plurality of solvent-containing sample vials, the apparatus comprising:
   (a) a heat-transmissive block having a top surface comprising a recessed sample chamber, the chamber comprising a plurality of well positions dimensioned to releasably hold sample vials in an upright, stable retained position within the chamber,
   (b) a positionable chamber cover dimensioned to form a air tight seal when in a closed positioned upon the chamber, the cover comprising a plurality of access apertures, each dimensioned to receive a respective air channeling device and positioned to lay in overlapping position with a respective well position when the cover is positioned upon the chamber, and
   (c) a vacuum circuit comprising a vacuum source attachment site associated with the block and a vacuum passageway operably connecting the source attachment site with the chamber,
   whereby, with solvent-containing vials in position within the chamber and air channeling devices in position within the aperture of the cover, and with the cover in position upon the chamber, then upon attachment of a vacuum source to the vacuum source attachment, a vacuum can be drawn in the sample chamber in order to correspondingly draw air through the air channeling devices such that air flow is directed toward the vial positions below in order to provide a blow-down evaporative effect.

2. An apparatus according to claim 1 wherein the chamber further comprises recessed well positions and a recessed rim at the block surface.

3. An apparatus according to claim 1 wherein the chamber is dimensioned to hold four vials.

4. An apparatus according to claim 1 wherein the apparatus is able to draw a vacuum of between about 20 mm and 700 mm Hg vacuum using a water aspirator.

5. An apparatus according to claim 1 further comprising a receptacle site for the insertion of a thermometer.

6. An evaporation system comprising a block according to claim 1 in combination with a heating block.

7. An evaporation system according to claim 6 further comprising air channeling devices selected from the group consisting of syringe needles and pipette tips.

8. An apparatus useful for evaporating solvent from a plurality of solvent-containing sample vials, the apparatus comprising:

a vacuum-tight sample chamber attachable to a vacuum source, and comprising sites for holding a plurality of solvent-containing vials within the chamber in a retained position, the chamber further comprising a cover portion providing a plurality of apertures in overlapping position to respective vial sites, and a plurality of air channeling devices positioned through the respective cover apertures, and above the vial sites within the chamber in order to provide air channels into the respective vials, whereby, with solvent-containing vials in position within the chamber and air channeling devices in position above the vial sites, the chamber can be attached to a vacuum source and a vacuum can be drawn in the sample chamber in order to correspondingly draw air through the air channeling devices such that air flow is directed toward the vial positions below in order to provide a blow-down evaporative effect.

9. An apparatus according to claim 8 wherein the chamber is dimensioned to hold four or more vials.

10. An apparatus according to claim 9 wherein the apparatus is able to draw a vacuum of between about 20 mm and 700 mm Hg vacuum using a water aspirator.

* * * * *